United States Patent
McDermott et al.

(10) Patent No.: US 7,335,631 B2
(45) Date of Patent: Feb. 26, 2008

(54) ENCAPSULATED PERFUME COMPOSITIONS IN HAIR AND SKIN PRODUCTS WHICH RELEASE A BURST OF FRAGRANCE AFTER INITIAL TOPICAL APPLICATION

(75) Inventors: Keith J. McDermott, Bound Brook, NJ (US); Zijie Judy Zhuang, Blue Bell, PA (US); Leslie C. Smith, Princeton, NJ (US)

(73) Assignee: Symrise, Inc., Teterboro, NJ (US)

( * ) Notice: Subject to any disclaimer, the term of this patent is extended or adjusted under 35 U.S.C. 154(b) by 477 days.

(21) Appl. No.: 10/238,386

(22) Filed: Sep. 9, 2002

(65) Prior Publication Data

US 2004/0048771 A1    Mar. 11, 2004

(51) Int. Cl.
*A61L 9/04*    (2006.01)
(52) U.S. Cl. .................................. 512/4; 512/1; 512/2
(58) Field of Classification Search ...................... 512/4
See application file for complete search history.

(56) References Cited

U.S. PATENT DOCUMENTS

| | | | |
|---|---|---|---|
| 3,516,941 A * | 6/1970 | Matson | 264/4.33 |
| 4,339,356 A * | 7/1982 | Whyte | 512/4 |
| 4,387,090 A | 6/1983 | Bolich, Jr. | 424/70 |
| 5,106,609 A | 4/1992 | Bolich, Jr. et al. | 424/70 |
| 5,112,688 A * | 5/1992 | Michael | 428/402.2 |
| 5,540,853 A | 7/1996 | Trinh et al. | 510/101 |
| 5,843,875 A | 12/1998 | Wei et al. | 510/101 |
| 5,849,310 A | 12/1998 | Trinh et al. | 424/401 |
| 6,045,835 A * | 4/2000 | Soper et al. | 426/89 |
| 6,149,898 A | 11/2000 | Peffy et al. | 424/70.12 |
| 6,194,375 B1 * | 2/2001 | Ness et al. | 512/4 |
| 6,207,141 B1 | 3/2001 | Pyles | 424/70.28 |
| 6,228,352 B1 | 5/2001 | Leet | 424/70.16 |
| 6,290,932 B2 | 9/2001 | Pratley et al. | 424/45 |
| 6,335,000 B1 | 1/2002 | Pratley | |
| 6,355,233 B1 | 3/2002 | Bergmann et al. | 424/70.12 |
| 6,620,777 B2 * | 9/2003 | Heibel et al. | 510/516 |
| 6,818,296 B1 * | 11/2004 | Garces Garces et al. | 428/402.2 |

FOREIGN PATENT DOCUMENTS

WO    95/16432    6/1995

* cited by examiner

*Primary Examiner*—Jill Warden
*Assistant Examiner*—Dwayne K. Handy
(74) *Attorney, Agent, or Firm*—Akerman Senterfitt; Stephan Pendorf; Gregory Lefkowitz

(57) ABSTRACT

The present invention relates to personal treatment compositions, which contain encapsulated perfume compositions, which release a burst of fragrance a period of time after initial topical application. According to the present invention, the burst of fragrance is released with the application of mechanical pressure on the encapsulated perfume composition. Further, the present invention relates to hair and skin compositions, which release a burst of fragrance a period of time after initial topical application by rubbing the skin or brushing the hair.

14 Claims, 1 Drawing Sheet

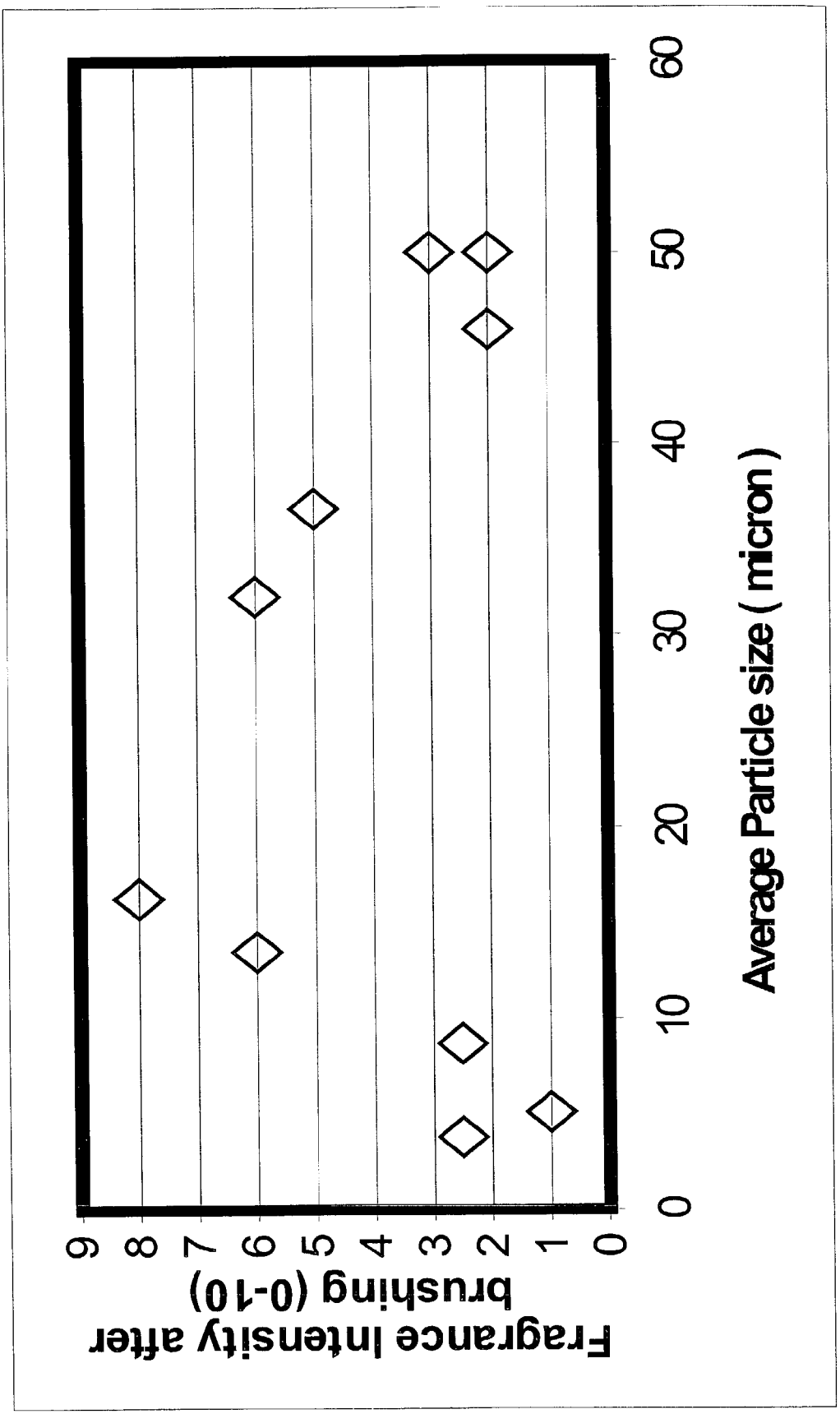

ENCAPSULATED PERFUME COMPOSITIONS IN HAIR AND SKIN PRODUCTS WHICH RELEASE A BURST OF FRAGRANCE AFTER INITIAL TOPICAL APPLICATION

FIELD OF THE INVENTION

The present invention relates to personal treatment compositions, which contain encapsulated perfume compositions, which release a burst of fragrance a period of time after initial topical application. According to the present invention, the burst of fragrance is released with the application of mechanical pressure on the encapsulated perfume composition. Further, the present invention relates to hair and skin compositions, which release a burst of fragrance a period of time after initial topical application by rubbing the skin, brushing the hair or touching the hair.

BACKGROUND OF THE INVENTION

Personal treatment compositions for topical application to the skin or hair, which also contain a perfume composition, are well known in the art. These include a wide variety of products such as lotions, shampoos conditioners and styling gels. In the late 1990's hair styling products accounted for approximately $270 million (16%) of the hair care industry.

Known personal treatment compositions can generally be divided into two categories, "rinse-off" and "leave-in" products. "Rinse-off" products include soaps, shampoos and conditioners. "Leave in" products include lotions, hair styling products and conditioners. These products may contain multiple fragrances and may release various fragrances noticeable to the user during their normal use, see for example U.S. Pat. No. 6,086,903 and WO 95/16432. WO 95/16432 discloses a cleaning composition with a dual blooming perfume system having a non-confined perfume and a confined perfume, wherein the confined perfume and the non-confined perfume have different fragrances and wherein the confined perfume fragrance is released as the user rubs the product (i.e., shampoo or conditioner) into their hair.

However, there remains a need for personal treatment compositions for the skin or hair that contain an encapsulated perfume composition, which can release a burst of fragrance, not during the initial topical application, but at other times during the day. This burst of fragrance can provide a signal to the consumer that their hair or skin product continues to work throughout the day, i.e., continues to release a pleasing fragrance. This burst of fragrance can be achieved by designing an encapsulation system that does not release an encapsulated fragrance during the product application phase but releases an encapsulated fragrance with the application of mechanical forces later in the day such as rubbing, blow drying or brushing.

SUMMARY OF THE INVENTION

The present invention relates to personal treatment compositions for the skin or hair that contain at least one free perfume oil, an encapsulated perfume composition containing at least one perfume oil, at least one conditioning agent and water. The encapsulated fragrance composition of the present invention has a wall material which is capable of remaining on the skin or hair following initial application and which is capable of later being sheared by the application of mechanical force. Accordingly, the encapsulated fragrance provides a "burst" of fragrance after initial topical application, when the user brushes their hair or rubs their skin.

BRIEF DESCRIPTION OF THE DRAWINGS

The FIGURE illustrates the fragrance intensity after brushing in relation to the average particle size of the encapsulated fragrance composition.

DETAILED DESCRIPTION OF THE INVENTION

The personal treatment composition of the present invention contains
 a) at least one free perfume oil,
 b) an encapsulated perfume composition, containing at least one perfume oil, wherein the encapsulated perfume composition is released by the application of mechanical force after the initial application,
 c) at least one conditioning agent, and
 d) water,
wherein the free perfume oil a) and the encapsulated perfume composition b) have a fragrance which is the same or different.

The term "free perfume oil" is understood to include perfume oils which are incorporated into the personal treatment compositions of the present invention without any substantial encapsulation or restriction material which would hinder the free perfume oil to release a fragrance upon exposure to the atmosphere.

The personal treatment composition of the present invention includes from about 0.01 to about 1.0 weight % of the free perfume oil, preferably 0.05 to about 0.2 weight % and about 0.1 to about 1.4 weight %, preferably about 0.7 to about 1.1 weight % of the encapsulated perfume composition, based on the total weight of the personal treatment composition. The weight percent of the encapsulated perfume compositions includes the encapsulation materials. The encapsulated perfume composition will preferably have a percentage of total perfume weight based upon the overall weight of the encapsulated perfume composition of from about 30 to about 90 weight %, preferably from about 60 to about 80 weight %. The encapsulated perfume composition has a diameter of about 10 to about 40 microns, preferably from about 15 to about 35 microns. The personal treatment compositions of the present invention include hair products or skin care products, which are not normally rinsed off after the initial topical application. Typical personal treatment compositions of the present invention include, for example, hair conditioners, hair sprays, hair gels, hair tonics, mousses, hair curlers, hair straighteners, skin lotions, spray on skin moisturizers, body sprays, skin moisturizers, skin softening lotions, suntan lotions, sun screen lotions, sunless tanning compositions, skin bleaching compositions, and topical pharmaceutical skin care compositions. Individual personal treatment compositions of the present invention contain a variety of components, which vary with product type and can be readily chosen by one skilled in the art.

The personal treatment compositions of the present invention contain at least one free perfume oil a), an encapsulated perfume composition containing at least one perfume oil b), at least one conditioning agent and water.

The following are non-limiting examples of perfume oil ingredients which are useful in the present invention: extracts from natural raw materials, such as, essential oils, concretes, absolutes, resins, resinoids, balsams, tinctures such as for example ambergris tincture; amyris oil; angelica seed oil; angelica root oil; aniseed oil; valerian oil; basil oil; tree moss absolute; bay oil; armoise oil; benzoe resinoid; bergamot oil; beeswax absolute; birch tar oil; bitter almond oil; savory oil; buchu leaf oil; cabreuva oil; cade oil; calamus oil; camphor oil; cananga oil; cardamom oil; cascarilla oil; cassia oil; cassie absolute; castoreum absolute; cedar leaf oil; cedar wood oil; cistus oil; citronella oil; lemon oil; copaiba balsam; copaiba balsam oil; coriander oil; costus root oil; cumin oil; cypress oil; davana oil; dill weed oil; dill seed oil; eau de brouts absolute; oakmoss absolute; elemi oil; estragon oil; eucalyptus citriodora oil; eucalyptus oil (cineole type); fennel oil; fir needle oil; galbanum oil; galbanum resin; geranium oil; grapefruit oil; guaiacwood oil; gurjun balsam; gurjun balsam oil; helichrysum absolute; helichrysum oil; ginger oil; iris root absolute; iris root oil; jasmine absolute; calamus oil; blue camomile oil; Roman camomile oil; carrot seed oil; cascarilla oil; pine needle oil; spearmint oil; caraway oil; labdanum oil; labdanum absolute; labdanum resin; lavandin absolute; lavandin oil; lavender absolute; lavender oil; lemon-grass oil; lovage oil; lime oil distilled; lime oil expressed; linaloe oil; Litsea cubeba oil; laurel leaf oil; mace oil; marjoram oil; mandarin oil; massoi (bark) oil; mimosa absolute; ambrette seed oil; musk tincture; clary sage oil; nutmeg oil; myrrh absolute; myrrh oil; myrtle oil; clove leaf oil; clove bud oil; neroli oil; olibanum absolute; olibanum oil; opopanax oil; orange flower absolute; orange oil; origanum oil; palmarosa oil; patchouli oil; perilla oil; Peru balsam oil; parsley leaf oil; parsley seed oil; petitgrain oil; peppermint oil; pepper oil; pimento oil; pine oil; pennyroyal oil; rose absolute; rosewood oil; rose oil; rosemary oil; Dalmatian sage oil; Spanish sage oil; sandal-wood oil; celery seed oil: spike-lavender oil; star anise oil; storax oil; tagetes oil; fir needle oil; tea tree oil; turpentine oil; thyme oil; Tolu balsam; tonka bean absolute; tuberose absolute; vanilla extract; violet leaf absolute; verbena oil; vetiver oil; juniperberry oil; wine lees oil; wormwood oil; wintergreen oil; ylang-ylang oil; hyssop oil; civet absolute; cinnamon leaf oil; cinnamon bark oil; and fractions thereof or ingredients isolated therefrom;

individual perfume ingredients from the group containing hydrocarbons, such as, for example, 3-carene; α-pinene; β-pinene; α-terpinene; γ-terpinene; p-cymene; bisabolene; camphene; caryophyllene; cedrene; farnesene; limonene; longifolene; myrcene; ocimene; valencene; (E,Z)-1,3,5-undecatriene; styrene; diphenylmethane;

aliphatic alcohols, such as, for example, hexanol; octanol; 3-octanol; 2,6-dimethylheptanol; 2-methyl-2-heptanol, 2-methyl-2-octanol; (E)-2-hexenol; (E)- and (Z)-3-hexenol; 1-octen-3-ol; a mixture of 3,4,5,6,6-pentamethyl-3/4-hepten-2-ol and 3,5,6,6-tetramethyl-4-methyleneheptan-2-ol; (E,Z)-2,6-nonadienol; 3,7-dimethyl-7-methoxyoctan-2-ol; 9-decenol; 10-undecenol; 4-methyl-3-decen-5-ol; aliphatic aldehydes and their acetals such as for example hexanal; heptanal; octanal; nonanal; decanal; undecanal; dodecanal; tridecanal; 2-methyloctanal; 2-methylnonanal; (E)-2-hexenal; (Z)-4-heptenal; 2,6-dimethyl-5-heptenal; 10-undecenal; (E)-4-decenal; 2-dodecenal; 2,6,10-trimethyl-5,9-undecadienal; heptanal-diethylacetal; 1,1-dimethoxy-2,2,5-trimethyl-4-hexene; citronellyl oxyacetaldehyde;

aliphatic ketones and oximes thereof, such as, for example, 2-heptanone; 2-octanone; 3-octanone; 2-nonanone; 5-methyl-3-heptanone; 5-methyl-3-heptanone oxime; 2,4,4,7-tetramethyl-6-octen-3-one; aliphatic sulfur-containing compounds, such as for example 3-methylthiohexanol; 3-methylthiohexyl acetate; 3-mercaptohexanol; 3-mercaptohexyl acetate; 3-mercaptohexyl butyrate; 3-acetylthiohexyl acetate; 1-menthene-8-thiol; aliphatic nitriles, such as for example 2-nonenenitrile; 2-tridecenenitrile; 2,12-tridecenenitrile; 3,7-dimethyl-2,6-octadienenitrile; 3,7-dimethyl-6-octenenitrile;

aliphatic carboxylic acids and esters thereof, such as, for example, (E)- and (Z)-3-hexenylformate; ethyl acetoacetate; isoamyl acetate; hexyl acetate; 3,5,5-trimethylhexyl acetate; 3-methyl-2-butenyl acetate; (E)-2-hexenyl acetate; (E)- and (Z)-3-hexenyl acetate; octyl acetate; 3-octyl acetate; 1-octen-3-yl acetate; ethyl butyrate; butyl butyrate; isoamyl butyrate; hexylbutyrate; (E)- and (Z)-3-hexenyl isobutyrate; hexyl crotonate; ethylisovalerate; ethyl-2-methyl pentanoate; ethyl hexanoate; allyl hexanoate; ethyl heptanoate; allyl heptanoate; ethyl octanoate; ethyl-(E,Z)-2,4-decadienoate; methyl-2-octinate; methyl-2-noninate; allyl-2-isoamyl oxyacetate; methyl-3,7-dimethyl-2,6-octadienoate;

acyclic terpene alcohols, such as, for example, citronellol; geraniol; nerol; linalool; lavandulol; nerolidol; farnesol; tetrahydrolinalool; tetrahydrogeraniol; 2,6-dimethyl-7-octen-2-ol; 2,6-dimethyloctan-2-ol; 2-methyl-6-methylene-7-octen-2-ol; 2,6-dimethyl-5,7-octadien-2-ol; 2,6-dimethyl-3,5-octadien-2-ol; 3,7-dimethyl-4,6-octadien-3-ol; 3,7-dimethyl-1,5,7-octatrien-3-ol 2,6-dimethyl-2,5,7-octatrien-1-ol; as well as formates, acetates, propionates, isobutyrates, butyrates, isovalerates, pentanoates, hexanoates, crotonates, tiglinates and 3-methyl-2-butenoates thereof;

acyclic terpene aldehydes and ketones, such as, for example, geranial; neral; citronellal; 7-hydroxy-3,7-dimethyloctanal; 7-methoxy-3,7-dimethyloctanal; 2,6,10-trimethyl-9-undecenal; α-sinensal; β-sinensal; geranylacetone; as well as the dimethyl- and diethylacetals of geranial, neral and 7-hydroxy-3,7-dimethyloctanal;

cyclic terpene alcohols, such as, for example, menthol; isopulegol; alpha-terpineol; terpinen-4-ol; menthan-8-ol; menthan-1-ol; menthan-7-ol; borneol; isoborneol; linalool oxide; nopol; cedrol; ambrinol; vetiverol; guaiol; and the formates, acetates, propionates, isobutyrates, butyrates, isovalerates, pentanoates, hexanoates, crotonates, tiglinates and 3-methyl-2-butenoates of alpha-terpineol; terpinen-4-ol; methan-8-ol; methan-1-ol; methan-7-ol; borneol; isoborneol; linalool oxide; nopol; cedrol; ambrinol; vetiverol; guaiol;

cyclic terpene aldehydes and ketones, such as, for example, menthone; isomenthone; 8-mercaptomenthan-3-one; carvone; camphor; fenchone; alpha-ionone; beta-ionone; alpha-n-methylionone; beta-n-methylionone; alpha-isomethylionone; beta-isomethylionone; alpha-irone; alpha-damascone; beta-damascone; beta-damascenone; delta-damascone; gamma-damascone; 1-(2,4,4-trimethyl-2-cyclohexen-1-yl)-2-buten-1-one; 1,3,4,6,7,8a-hexahydro-1,1,5,5-tetramethyl-2H-2,4a-methanonaphthalen-8(5H)-one; nootkatone; dihydronootkatone; acetylated cedarwood oil (cedryl methyl ketone);

cyclic alcohols, such as, for example, 4-tert.-butylcyclohexanol; 3,3,5-trimethylcyclohexanol; 3-isocamphylcyclohexanol; 2,6,9-trimethyl-Z2,Z5,E9-cyclododecatrien-1-ol; 2-isobutyl-4-methyltetrahydro-2H-pyran-4-ol;

cycloaliphatic alcohols, such as, for example, alpha, 3,3-trimethylcyclo-hexylmethanol; 2-methyl-4-(2,2,3-trimethyl-3-cyclopent-1-yl)butanol; 2-methyl-4-(2,2,3-trimethyl-3-cyclopent-1-yl)-2-buten-1-ol; 2-ethyl-4-(2,2,3-trimethyl-3-cyclopent-1-yl)-2-buten-1-ol; 3-methyl-5-(2,2,3-trimethyl-3-cyclopent-1-yl)-pentan-2-ol; 3-methyl-5-(2,2,3-trimethyl-3-cyclopent-1-yl)-4-penten-2-ol; 3,3-dimethyl-5-(2,2,3-trimethyl-3-cyclopent-1-yl)-4-penten-2-ol; 1-(2,2,6-trimethylcyclohexyl)pentan-3-ol; 1-(2,2,6-trimethylcyclohexyl)hexan-3-ol;

cyclic and cycloaliphatic ethers, such as, for example, cineole; cedryl methyl ether; cyclododecyl methyl ether; (ethoxymethoxy)cyclododecane; alpha-cedrene epoxide; 3a,6,6,9a-tetramethyldodecahydronaphtho[2,1-b]furan; 3a-ethyl-6,6,9a-trimethyldodecahydronaphtho[2,1-b]furan; 1,5,9-trimethyl-13-oxabicyclo[10.1.0]-trideca-4,8-diene; rose oxide; 2-(2,4-dimethyl-3-cyclohexen-1-yl)-5-methyl-5-(1-methylpropyl)-1,3-dioxan;

cyclic ketones, such as, for example, 4-tert.-butylcyclohexanone; 2,2,5-trimethyl-5-pentylcyclopentanone; 2-heptylcyclopentanone; 2-pentylcyclopentanone; 2-hydroxy-3-methyl-2-cyclopenten-1-one; 3-methyl-cis-2-penten-1-yl-2-cyclopenten-1-one; 3-methyl-2-pentyl-2-cyclopenten-1-one; 3-methyl-4-cyclopentadecenone; 3-methyl-5-cyclopentadecenone; 3-methylcyclopentadecanone; 4-(1-ethoxyvinyl)-3,3,5,5-tetramethylcyclohexanone; 4-tert.-pentylcyclohexanone; 5-cyclohexadecen-1-one; 6,7-dihydro-1,1,2,3,3-pentamethyl-4(5H)-indanone; 5-cyclohexadecen-1-one; 8-cyclohexadecen-1-one; 9-cycloheptadecen-1-one; cyclopentadecanone;

cycloaliphatic aldehydes, such as, for example, 2,4-dimethyl-3-cyclohexene carbaldehyde; 2-methyl-4-(2,2,6-trimethyl-cyclohexen-1-yl)-2-butenal; 4-(4-hydroxy-4-methylpentyl)-3-cyclohexene carbaldehyde; 4-(4-methyl-3-penten-1-yl)-3-cyclohexene carbaldehyde;

cycloaliphatic ketones, such as, for example, 1-(3,3-dimethylcyclohexyl)-4-penten-1-one; 1-(5,5-dimethyl-1-cyclohexen-1-yl)-4-penten-1-one; 2,3,8,8-tetramethyl-1,2,3,4,5,6,7,8-octahydro-2-naphtalenyl methyl-ketone; methyl-2,6,10-trimethyl-2,5,9-cyclododecatrienyl ketone; tert.-butyl-(2,4-dimethyl-3-cyclohexen-1-yl)ketone;

esters of cyclic alcohols, such as, for example, 2-tert.-butylcyclohexyl acetate; 4-tert.-butylcyclohexyl acetate; 2-tert.-pentylcyclohexyl acetate; 4-tert.-pentylcyclohexyl acetate; decahydro-2-naphthyl acetate; 3-pentyltetrahydro-2H-pyran-4-yl acetate; decahydro-2,5,5,8a-tetramethyl-2-naphthyl acetate; 4,7-methano-3a,4,5,6,7,7a-hexahydro-5 or 6-indenyl acetate; 4,7-methano-3a,4,5,6,7,7a-hexahydro-5 or 6-indenyl propionate; 4,7-methano-3a,4,5,6,7,7a-hexahydro-5 or 6-indenyl-isobutyrate; 4,7-methanooctahydro-5 or 6-indenyl acetate;

esters of cycloaliphatic carboxylic acids, such as, for example, allyl 3-cyclohexyl-propionate; allyl cyclohexyl oxyacetate; methyl dihydrojasmonate; methyl jasmonate; methyl 2-hexyl-3-oxocyclopentanecarboxylate; ethyl 2-ethyl-6,6-dimethyl-2-cyclohexenecarboxylate; ethyl 2,3,6,6-tetramethyl-2-cyclohexenecarboxylate; ethyl 2-methyl-1,3-dioxolane-2-acetate;

araliphatic alcohols, such as, for example, benzyl alcohol; 1-phenylethyl alcohol; 2-phenylethyl alcohol; 3-phenylpropanol; 2-phenylpropanol; 2-phenoxyethanol; 2,2-dimethyl-3-phenylpropanol; 2,2-dimethyl-3-(3-methylphenyl)propanol; 1,1-dimethyl-2-phenylethyl alcohol; 1,1-dimethyl-3-phenylpropanol; 1-ethyl-1-methyl-3-phenylpropanol; 2-methyl-5-phenylpentanol; 3-methyl-5-phenylpentanol; 3-phenyl-2-propen-1-ol; 4-methoxybenzyl alcohol; 1-(4-isopropylphenyl)ethanol;

esters of araliphatic alcohols and aliphatic carboxylic acids, such as, for example, benzyl acetate; benzyl propionate; benzyl isobutyrate; benzyl isovalerate; 2-phenylethyl acetate; 2-phenylethyl propionate; 2-phenylethyl isobutyrate; 2-phenylethyl isovalerate; 1-phenylethyl acetate; alpha-trichloromethylbenzyl acetate; alpha, alpha-dimethylphenylethyl acetate; alpha, alpha-dimethylphenylethyl butyrate; cinnamyl acetate; 2-phenoxyethyl isobutyrate; 4-methoxybenzyl acetate; araliphatic ethers, such as for example 2-phenylethyl methyl ether; 2-phenylethyl isoamyl ether; 2-phenylethyl-1-ethoxyethyl ether; phenylacetaldehyde dimethyl acetal; phenylacetaldehyde diethyl acetal; hydratropaaldehyde dimethyl acetal; phenylacetaldehyde glycerol acetal; 2,4,6-trimethyl-4-phenyl-1,3-dioxane; 4,4a,5,9b-tetrahydroindeno[1,2-d]-m-dioxin; 4,4a,5,9b-tetrahydro-2,4-dimethylindeno[1,2-d]-m-dioxin;

aromatic and araliphatic aldehydes, such as, for example, benzaldehyde; phenylacetaldehyde; 3-phenylpropanal; hydratropaldehyde; 4-methylbenzaldehyde; 4-methylphenylacetaldehyde; 3-(4-ethylphenyl)-2,2-dimethylpropanal; 2-methyl-3-(4-isopropylphenyl)propanal; 2-methyl-3-(4-tert.-butylphenyl)propanal; 3-(4-tert.-butylphenyl)propanal; cinnamaldehyde; alpha-butylcinnamaldehyde; alpha-amylcinnamaldehyde; alpha-hexylcinnamaldehyde; 3-methyl-5-phenylpentanal; 4-methoxybenzaldehyde; 4-hydroxy-3-methoxybenzaldehyde; 4-hydroxy-3-ethoxybenzaldehyde; 3,4-methylene-dioxybenzaldehyde; 3,4-dimethoxybenzaldehyde; 2-methyl-3-(4-methoxyphenyl)propanal; 2-methyl-3-(4-methylendioxyphenyl)propanal;

aromatic and araliphatic ketones, such as, for example, acetophenone; 4-methylacetophenone; 4-methoxyacetophenone; 4-tert.-butyl-2,6-dimethylacetophenone; 4-phenyl-2-butanone; 4-(4-hydroxyphenyl)-2-butanone; 1-(2-naphthalenyl)ethanone; benzophenone; 1,1,2,3,3,6-hexamethyl-5-indanyl methyl ketone; 6-tert.-butyl-1,1-dimethyl-4-indanyl methyl ketone; 1-[2,3-dihydro-1,1,2,6-tetramethyl-3-(1-methyl-ethyl)-1H-5-indenyl]ethanone; 5',6',7',8'-tetrahydro-3',5',5',6',8',8'-hexamethyl-2-acetonaphthone;

aromatic and araliphatic carboxylic acids and esters thereof, such as, for example, benzoic acid; phenylacetic acid; methyl benzoate; ethyl benzoate; hexyl benzoate; benzyl benzoate; methyl phenylacetate; ethyl phenylacetate; geranyl phenylacetate; phenylethyl phenylacetate; methyl cinnamate; ethyl cinnamate; benzyl cinnamate; phenylethyl cinnamate; cinnamyl cinnamate; allyl phenoxyacetate; methyl salicylate; isoamyl salicylate; hexyl salicylate; cyclohexyl salicylate; cis-3-hexenyl salicylate; benzyl salicylate; phenylethyl salicylate; methyl 2,4-dihydroxy-3,6-dimethylbenzoate; ethyl 3-phenylglycidate; ethyl 3-methyl-3-phenylglycidate;

nitrogen-containing aromatic compounds, such as, for example, 2,4,6-trinitro-1,3-dimethyl-5-tert.-butylbenzene; 3,5-dinitro-2,6-dimethyl-4-tert.-butylacetophenone; cinnamonitrile; 5-phenyl-3-methyl-2-pentenonitrile; 5-phenyl-3-methylpentanonitrile; methyl anthranilate; methy-N-methylanthranilate; Schiff's bases of methyl anthranilate with 7-hydroxy-3,7-dimethyloctanal, 2-methyl-3-(4-tert.-butylphenyl)propanal or 2,4-dimethyl-3-cyclohexene carbaldehyde; 6-isopropylquinoline; 6-isobutylquinoline; 6-sec.-butylquinoline; indole; skatole; 2-methoxy-3-isopropylpyrazine; 2-isobutyl-3-methoxypyrazine;

phenols, phenyl ethers and phenyl esters, such as, for example, estragole; anethole; eugenol; eugenyl methyl ether; isoeugenol; isoeugenol methyl ether; thymol; carvacrol; diphenyl ether; beta-naphthyl methyl ether; beta-naphthyl ethyl ether; beta-naphthyl isobutyl ether; 1,4-dimethoxybenzene; eugenyl acetate; 2-methoxy-4-methylphenol; 2-ethoxy-5-(1-propenyl)phenol; p-cresyl phenylacetate;

heterocyclic compounds, such as, for example, 2,5-dimethyl-4-hydroxy-2H-furan-3-one; 2-ethyl-4-hydroxy-5-methyl-2H-furan-3-one; 3-hydroxy-2-methyl-4H-pyran-4-one; 2-ethyl-3-hydroxy-4H-pyran-4-one;

lactones, such as, for example, 1,4-octanolide; 3-methyl-1,4-octanolide; 1,4-nonanolide; 1,4-decanolide; 8-decen-1,4-olide; 1,4-undecanolide; 1,4-dodecanolide; 1,5-decanolide; 1,5-dodecanolide; 1,15-pentadecanolide; cis- and trans- 11-pentadecen-1,15-olide; cis- and trans-12-pentadecen-1,15-olide; 1,16-hexadecanolide; 9-hexadecen-1,16-olide; 10-oxa-1,16-hexadecanolide; 11-oxa-1,16-hexadecanolide; 12-oxa-1,16-hexadecanolide; ethylene-1,12-dodecanedioate; ethylene-1,13-tridecanedioate; coumarin; 2,3-dihydrocoumarin; octahydrocoumarin.

The perfume oil may also contain materials having no odor or very faint odor, which are known as diluents or extenders. Non-limiting examples of these materials are dipropylene glycol, diethyl phthalate, triethyl citrate, isopropyl myristate, and benzyl benzoate. These materials are used for diluting and stabilizing some other perfume ingredients. These diluents are considered to be additional ingredients and not considered as a fragrance ingredient.

The encapsulated perfume composition contains at least one perfume oil as described above which is encapsulated by an encapsulation material. The encapsulated perfume composition b) has a fragrance, which can be the same or different from free perfume oil a). The fragrance of free perfume oil a) is released when the container is opened to dispense the personal treatment composition and when the personal treatment composition is initially applied to the hair or skin. The fragrance of the encapsulated perfume composition b) is released a period of time after initial application when a sufficient mechanical force has been applied to the skin or hair.

The encapsulated fragrance composition b) of the present invention has an encapsulation wall material, which is capable of remaining on the skin or hair following initial application, is not broken or damaged by the initial topical application and which is capable of later being sheared by the application of mechanical force thereby releasing the encapsulated fragrance a period of time after initial application.

The encapsulated perfume composition b) should be sufficiently encapsulated in the wall material as to not allow a significant amount of the encapsulated perfume fragrance to be dispensed when the personal treatment composition is poured from its packaging container or when initially topically applied.

The encapsulation material should be insoluble in water and remain intact during processing, packaging, shipment, storage and initial topical application; however, the encapsulation wall material should be capable of later being sheared by the application of mechanical force, thereby releasing a fragrance.

The encapsulation wall material can be any suitable film forming material which is water insoluble and which is reasonably impervious to the perfume oil but which is capable of being sheared after the initial topical application via a mechanical force. Suitable polymeric materials include polyurethane, polyamide, polyester, silicone resin, epoxy resin, urea-formaldehyde and proteins, such as gelatin, casein and serum albumen. The encapsulation wall material can include reactive products urea and aldehyde, such as formaldehyde. Preferable materials include those capable of acid condition polymerization from a water-soluble prepolymer state. Such prepolymers can be made by reacting urea and formaldehyde in a formaldehyde: urea molar ratio of from about 1.2:1 to about 2.6:1. Thiourea, cyanuramide, guanidine, N-alkyl ureas, phenols, sulfonamides, anilines and mines can be included in small amounts as modifiers for the urea.

The encapsulation wall can be made by any method known to those skilled in the art, such as coacervation and interfacial polymerization. Generally the encapsulation wall can be prepared by any conventional process, which produces capsules of the proper size and resistance. Preferably, the encapsulation wall is made from urea-formaldehyde shell materials and is produced by an interfacial polymerization process described in U.S. Pat. No. 3,516,941, the teachings of which are incorporated by reference. As taught in U.S. Pat. No. 3,516,941, an aqueous solution of a urea-formaldehyde precondensate (methylol urea or PMU) is formed containing from about 3% to about 40% by weight of the precondensate. The perfume oil is dispersed throughout the aqueous solution in the form of microscopically sized discreet droplets. While maintaining a solution temperature between 20° C. and 90° C. acid is then added to catalyze polymerization of the disclosed urea-aldehyde precondensate. If the solution is rapidly agitated during this polymerization step, shells of water insoluble urea-formaldehyde polymer form around and encapsulate the perfume oil. The encapsulated perfume composition will preferably have a percentage of total perfume weight based upon the overall weight of the encapsulated perfume composition of from about 30 to about 90 weight %, preferably from about 60 to about 80 weight %. The encapsulated perfume composition has a diameter of about 10 to about 40 microns, preferably from about 15 to about 35 microns.

The personal treatment compositions for the skin and hair according to the present invention also include standard components in standard amounts known to those skilled in the art. Examples of such components include, surfactants, such as anionic surfactants, nonionic surfactants, amphoteric surfactants and mixtures thereof, neutralizing agents and/or pH adjusters, conditioning agents, such as silicone conditioning agents, cationic polymer conditioning agents, hydrocarbon, ester and alcohol conditioning agents, adhesive polymers, solvents, pharmaceutical agents, carriers, thickening agents, suspending agents, emollients, emulsifiers, solubilizers, propellants, solvents, humectants, liposomes, preservatives, chelating agents, and setting polymers. Suitable such components are disclosed in U.S. Pat. Nos. 5,510,12; 5,106,609; 6,290,932; 6,355,233; 6,149,898; 6,228,352; 4,387,090; 6,207,141; 6,335,000; 5,843,875; 5,540,853 and U.S. Pat. No. 5,849,310, the teachings of which are incorporated herein by reference. Preferred solvents include alcohol and water. Preferred setting polymers include polyurethane-1, triethyl citrate, PVA/MA copolymers and polyacrylamide. Preferred conditioning agents include panthenol, dimethicone copolyol, phytantriol, stearamidopropyl dimethylamine, tallowtrimonium chloride, nonoxynol-10, polyquaternium-7 and cyclomethicone. Dimethyl ether and hydrocarbons are preferred propellants. Preferred preservatives include methylchloro isothiazolinone, methylisothiazole, triclosan and teatrasodium EDTA. Preferred humectants include propylene glycol, glycerin and panthenol. Preferred pH adjusters include aminomethyl propanediol, citric acid and thriethanolamine. Preferred solubilizers and emulsifiers are laureth-7, ethoxylated alcohols, ethoxylated sorbitan esters and ethoxylated hydrogenated castor oil. Preferred thickeners include stearic acid, cetyl alcohol and acrylate copolymers. Preferred emollients include mineral oil, glycol stearate, isostearyl neopentonate, dimethicone, isoparaffin and capric triglyceride.

The invention is further illustrated but is not intended to be limited by the following examples in which all parts and percentages are by weight unless otherwise specified.

EXAMPLES

Preparation of a Personal Treatment Composition:

Eleven leave-in conditioner samples were prepared each containing an encapsulated fragrance. The samples varied in the particle diameter of the encapsulated fragrance and the type of wall material used. The samples were prepared by mixing Part A and Part B in separate mixing vessels and heating the vessels to 75° C. Then while stirring Part A was added to Part B to form Part AB. Next Part C was mixed in a separate vessel and heated to 70° C. Then Part AB was added to Part C. Finally, the mixture was cooled down to room temperature and continuously agitated while the encapsulated fragrance was added. Table 1 illustrates the leave-in conditioner formulation prepared.

TABLE 1

| INGREDIENT | WEIGHT PERCENT (wt. %) |
|---|---|
| PART A | |
| Diacetyldimonium Chloride (Varisoft 432 CG, commercially available from Witco) | 0.50 |
| Cyclomethicone (Cyclomethicone 344, commercially available from Dow Corning) | 0.10 |
| PART B | |
| Stearamidopropyl Dimethylamine (Lexamine S-13, commercially available from Inolex) | 0.40 |
| Deionized Water | 92.05 |
| Citric Acid | 0.05 |
| PART C | |
| Deionized Water | 4.90 |
| Panthenol (D,L-Panthenol, commercially available from Jesen) | 0.20 |
| Amodimethicone, tallow, trimonium chloride and nonoxynol-10 (929 Cationic Emulsion) | 1.50 |

Fragrance Intensity Test:

A 35 g virgin Asian hair swatch was washed with unfragranced shampoo, then 2 grams of the leave-in conditioner, according to Table 1, was applied to the wet hair swatch, each containing an encapsulated perfume composition, prepared in accordance to U.S. Pat. No. 3,516,941. Table 2 illustrates the properties of the encapsulated perfume composition. The swatch was then evaluated for fragrance intensity by a panel of 6 experts. Each panelist rated the fragrance intensity on a scale of 0-10 with 10 being the highest intensity. The ratings of each panelist were then averaged. The hair swatch was then blow dried and evaluated. The hair was allowed to age overnight and evaluated again. The hair was then brushed and evaluated immediately. The results of the Fragrance Intensity Test appear in Table 3 and the Figure.

TABLE 2

| Sample | Wall Material | Size Microns | % Fragrance in Slurry | % Slurry in Base | % Encapsulated Fragrance |
|---|---|---|---|---|---|
| A | None - free perfume oil only | NA | NA | NA | 0.6% free oil |
| B | PMU | 16.3 | 21.4 | 2.8 | 0.6% encapsulated oil |
| C | PMU | 32.0 | 21.4 | 2.8 | 0.6% encapsulated oil |
| D | Gelatin-GA | 50.0 | 36.0 | 1.7 | 0.6% encapsulated oil |
| E | PMU | 8.7 | 21.4 | 2.8 | 0.6% encapsulated oil |
| F | Melamine | 50.0 | 40.0 | 1.5 | 0.6% encapsulated oil |
| G | Melamine | 5.1 | 40.0 | 1.5 | 0.6% encapsulated oil |
| H | Melamine | 3.8 | 40.0 | 1.5 | 0.6% encapsulated oil |
| I | PMU | 13.5 | 40.0 | 1.5 | 0.6% encapsulated oil |
| J | PMU | 36.6 | 21.4 | 2.8 | 0.6% encapsulated oil |
| K | PMU | 46.0 | 21.4 | 2.8 | 0.6% encapsulated oil |

TABLE 3

| Sample | Wall Material | Size | Bottle | Wet Hair | Dry Hair | Aged hair 16 hrs. before brushing | After Brushing |
|---|---|---|---|---|---|---|---|
| A | None - free perfume oil only | NA | 7 | 5 | 3 | 2 | 2 |
| B | PMU | 16.3 | 7 | 5 | 2.5 | 1.5 | 8 |
| C | PMU | 32.0 | 6.5 | 4.5 | 3 | 1.5 | 6 |
| D | Gelatin-GA | 50.0 | 7.5 | 5 | 4 | 2.5 | 3 |
| E | PMU | 8.7 | 7 | 5 | 3.5 | 1 | 2.5 |
| F | Melamine | 50.0 | 7 | 4 | 2.5 | 1.2 | 2 |
| G | Melamine | 5.1 | 7 | 4.5 | 3.5 | 1 | 1 |
| H | Melamine | 3.8 | 7 | 5 | 3.5 | 1.5 | 2.5 |
| I | PMU | 13.5 | 5 | 4 | 4 | 1.5 | 6 |
| J | PMU | 36.6 | 5 | 4 | 3.5 | 2 | 5 |
| K | PMU | 46.0 | 5 | 3 | 3 | 1 | 2 |

The data in Table 3 illustrates that encapsulated perfume compositions having a diameter smaller than 10 microns or larger than 40 microns do not impart a fragrance "burst" from the hair sample.

Comparative Example

Samples of a shampoo and conditioner containing about 50 micron size gelatin capsules were prepared by a similar procedure to Example 1 in WO 95/16432 except that gum arabic was used to prepare the encapsulated fragrance composition rather than sodium hexametampolyphosphate. The shampoos and conditioners contained either 0.6% encapsulated fragrance or 0.6% fragrance oil as a control. 3 grams of the shampoo was applied to a 35 gram hair swatch and evaluated after the product was rubbed into the hair and after rinsing. 3 grams of conditioner was then applied and evaluated when rubbed into the hair, after rinsing, during blow drying (in the air), 4 hours after the hair was dry and after the hair was brushed. Each evaluation was performed by 6 sensory evaluation experts and each expert rated the fragrance intensity on a scale of 0-10 with 10 being the highest intensity. The results were averaged and displayed in the Table 4 below.

TABLE 4

| Samples used | Lathering (rubbing) | Shampoo Rinse | Conditioner rubbed into hair | Conditioner rinse | Blow dry | 4 hr | Brush |
|---|---|---|---|---|---|---|---|
| Fruity Fragrance oil 0.6% | 7 | 4.5 | 6 | 4 | 6.5 | 3.5 | 3.5 |
| Encapsulated Fruity Fragrance 0.6% | 5.5 | 4 | 5.5 | 5.5 | 4 | 3 | 3 |

The similar intensities between the shampoo with free fragrance oil compared to encapsulated fragrance oil indicates that the encapsulation system, according to WO 95/16432, releases most or all of the fragrance when rubbed or worked into the hair. The evaluation of the conditioner samples when rubbed into the hair yield similar results again showing that the encapsulation breaks and releases the perfume. When the dry hair is brushed 4 hours later, no burst effect is observed. Therefore, the encapsulation system according to WO 95/16432 is not capable of delivering the effect as disclosed in the present invention.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A personal treatment composition useful for topical application comprising: a) at least one free perfume oil, b) an encapsulated perfume composition comprising at least one perfume oil, wherein the encapsulated perfume composition is released by the application of mechanical force after the initial, topical application, and wherein he encapsulated perfume composition has a diameter of 10 to 40 microns, c) at least one conditioning agent, d) water, and wherein the free perfume oil a) and the encapsulated perfume composition b) have a fragrance which is the same or different; and, the encapsulated perfume composition comprises a wall material, wherein the wall material is PMU.

2. The personal treatment composition according to claim 1, wherein the perfume oil accounts for about 30 to about 90 weight % of the total weight of the encapsulated perfume composition.

3. The personal treatment composition according to claim 1, wherein the encapsulated perfume composition has a diameter of about 15 to about 35 microns.

4. The personal treatment composition according to claim 1, wherein the encapsulated perfume composition accounts for from about 0.1 wt. % to about 1.4 wt. % of the total personal care composition.

5. The personal treatment composition according to claim 4, wherein the encapsulated perfume composition accounts for from about 0.7 wt. % to about 1.1 wt. % of the total personal care composition.

6. The personal treatment composition according to claim 1, wherein the free perfume oil accounts for about 0.01 wt. % to about 1.0 wt. % of the total personal care composition.

7. The personal treatment composition according to claim 6, wherein the free perfume oil accounts for about 0.05 wt. % to about 0.1 wt. % of the total personal care composition.

8. The personal treatment composition according to claim 1, wherein the conditioning agent is selected from the group consisting of dicetyldimonium chloride, phanthenol, amodimethicone, tallow, trimonium chloride and nonolynol-10.

9. The personal treatment composition according to claim 1, wherein the personal treatment composition is a lotion, a cream, a leave-in conditioner, a hair gel, a hair mouse, or a hair spray.

10. The personal treatment composition according to claim 1, wherein the free perfume oil a) and the encapsulated perfume composition b) have a fragrance which is different.

11. A hair care product comprising: a) at least one free perfume oil b) an encapsulated perfume composition comprising at least one perfume oil, wherein the encapsulated perfume composition is released by the application of mechanical force after the initial application to the hair, and wherein the encapsulated perfume composition has a diameter of about 10 to about 40 microns, c) at least one cationic agent, d) at least one topical carrier, e) at least one conditioning agent, f) at least one surfactant, and g) at least one neutralizer, wherein the perfume oil a) and the encapsulated perfume composition b) have a fragrance which is the same or different, and wherein the encapsulated perfume composition comprises a wall material, wherein the wall material is PMU.

12. A skin product comprising: a) at least one perfume oil, b) an encapsulated perfume composition comprising at least one perfume oil, wherein the encapsulated perfume composition is released by the application of mechanical force after the initial application to the skin, and wherein the encapsulated perfume composition has a diameter of about 10 to about 40 microns, c) at least one moisturizer, d) at least one emollient, e) water, f) at least one skin conditioning agent, and g) at least one neutralizer, wherein the perfume oil a) and the encapsulated perfume composition b) have a fragrance which is the same or different, and wherein the encapsulated perfume composition comprises a wall material, wherein the wall material is PMU.

13. A skin care product comprising:
a) at least one perfume oil;
b) an encapsulated perfumer composition comprising at least one perfume oil, wherein the encapsulated perfume composition is released by the application of mechanical force after the initial application to the skin;
c) at least one pharmaceutical agent;
d) water;
e) at least one emollient wherein,
the perfume oil a) and the encapsulated perfume composition b) have a fragrance which is the same or different, wherein the encapsulated perfume composition is released by the application of mechanical force after the initial application to the skin, and wherein the encapsulated perfume composition has a diameter of about 10 to about 40 microns, wherein the encapsulated perfume composition comprises a wall material, and the wall material is PMU.

14. The skin product in claim 13, where the pharmaceutical agent is an antiperspirant active.

* * * * *